US005779833A

United States Patent [19]
Cawley et al.

[11] Patent Number: 5,779,833
[45] Date of Patent: Jul. 14, 1998

[54] METHOD FOR CONSTRUCTING THREE DIMENSIONAL BODIES FROM LAMINATIONS

[75] Inventors: James D. Cawley. Shaker Heights; Arthur H. Heuer. Cleveland; Wyatt S. Newman. Cleveland Heights. all of Ohio

[73] Assignee: Case Western Reserve University. Cleveland, Ohio

[21] Appl. No.: 631,378

[22] Filed: Apr. 12, 1996

Related U.S. Application Data

[63] Continuation-in-part of Ser. No. 511,604, Aug. 4, 1995, abandoned.

[51] Int. Cl.$^6$ .............................. B32B 31/06; B32B 31/26
[52] U.S. Cl. .................. 156/89.11; 156/263; 156/308.6; 264/610
[58] Field of Search ................................. 156/58, 59, 63, 156/89, 155, 246, 252, 256, 263, 264, 267, 77, 308.6; 264/56, 44, 45.1, 59, 43, 610, 642

[56] References Cited

U.S. PATENT DOCUMENTS 2,556,798  6/1951  Concordet.
3,932,923  1/1976  DiMatteo.

(List continued on next page.)

OTHER PUBLICATIONS

Proposal dated Aug. 31, 1993 in Response to ARPA BAA 93–24 entitled Computer–Aided Manufacturing of Laminated Engineering Materials.
Proposal dated Feb. 9, 1994 to the Office of Naval Research and to ARPA/DSO entitled Processing of Ceramic Composites Using Laminated Object Manufacturing (LOM) Technology.
Proposal dated Apr. 7, 1994 in Response to Solicitation No. DOE/ER–0605 entitled CAM–LEM: Computer–Aided Manufacturing of Laminated Engineering Materials.
Proposal circa Apr. 1994 in Response to DOD STTR program concerning Topic No. ARMY 94T003 entitled CAM–LEM: Computer–Aided Manufacturing of Laminated Engineering Materials.
Laser CIM In 3–D–Complex Objects Production by Michael Feygin, Industrial Laser Review—Jun. 1987.
Three–Dimensional Printing dated Apr. 28, 1988 by Norman Kinzie pp. 1–23.
1987 Manufacturing Technology Review NAMRC XV Proceedings Copyright 1987, pp. 637–640.
Advanced Technology of Plasticity 1984: vol. I—Proceedings of The First International Conference on Technology of Plasticity Tokyo, 1984, pp. 520–525.
Proposal dated Sep. 19, 1994—Response to NSF 94–63 entitled "Rapid Prototyping: Virtual and Physical".

*Primary Examiner*—Curtis Mayes
*Attorney, Agent, or Firm*—Fay, Sharpe, Beall, Fagan, Minnich & McKee

[57] ABSTRACT

A method for manufacturing an integral three dimensional object from laminations includes the steps of fabricating a plurality of first sheets of a first material composition, cutting each of the first sheets to form a contoured layer representing a cross-section of the three dimensional object and to form a waste material and discarding the waste material. The contoured layers are stacked in a desired sequence to form a stack of contoured layers which are then laminated. Subsequently, the contoured layers of the stack are secured to each other to form the integral three dimensional object. This method works particularly well with ceramic material sheets. If desired, a second type of sheet made of a fugitive material can also be cut to form a contoured layer representing a void in a cross-section of the three dimensional object. The contoured layers of the second sheets are then stacked along with the contoured layers of the first sheets to form the object. The laminated stack of contoured layers is then sintered. During processing, fugitive material can be removed, leaving voids in the three dimensional object.

16 Claims, 4 Drawing Sheets

U.S. PATENT DOCUMENTS

| | | |
|---|---|---|
| 4,323,756 | 4/1982 | Brown et al. . |
| 4,752,352 | 6/1988 | Feygin . |
| 4,863,538 | 9/1989 | Deckard . |
| 4,961,154 | 10/1990 | Pomerantz et al. . |
| 5,015,312 | 5/1991 | Kinzie . |
| 5,031,483 | 7/1991 | Weaver . |
| 5,053,093 | 10/1991 | Ciccarelli et al. .................... 264/59 X |
| 5,071,503 | 12/1991 | Berman ................................ 156/264 X |
| 5,094,935 | 3/1992 | Vassiliou et al. . |
| 5,174,843 | 12/1992 | Natter . |
| 5,271,150 | 12/1993 | Inasaka ................................. 156/89 X |
| 5,354,414 | 10/1994 | Feygin . |
| 5,398,193 | 3/1995 | deAngelis . |
| 5,514,232 | 5/1996 | Burns ........................................ 156/64 |
| 5,601,673 | 2/1997 | Alexander ................................. 156/89 |

METHOD FOR CONSTRUCTING THREE DIMENSIONAL BODIES FROM LAMINATIONS

This application is a continuation-in-part of application Ser. No. 08/511.604 which was filed on Aug. 4, 1995, now abandoned.

BACKGROUND OF THE INVENTION

This invention generally relates to solid freeform fabrication (SFF) apparatus and methods, as well as products manufactured thereby. More particularly, the present invention relates to a method and apparatus for manufacturing an integral three dimensional object which is formed from individually contoured laminations of gradually varying shape.

There has been much recent discussion concerning the feasibility of building a flexible system for automatically manufacturing three dimensional prototypes and products. Prototyping was originally conceived as a method for automated model making from computer-aided design descriptions of complex parts. Such prototyping is now included under the more general term "solid freeform fabrication (SFF)." SSF includes automatic fabrication of functional prototypes and actual production of small numbers of engineering components. Most of the current approaches, however, involve simultaneous materials processing and shape generation. This results in a compromise between geometrical accuracy and the structural behavior of the parts produced.

It has been determined that a three dimensional object can be produced more accurately by utilizing thin plane cross-sections of a solid body as its building blocks with each of the cross-sections being cut or formed separately. Each cross-section can be cut by a laser located above a positioning or platter-like table. The several cross-sections are then attached to each other using suitable bonding techniques.

This technology would appear to be available to any class of engineering materials available in sheet form and for which monolithic components are desired. Such materials include metals and alloys, engineering polymers and plastics, composites, ceramics and the like. Moreover, laminated composites of dissimilar materials (such as metals and ceramics, tough components with wear-resistant surfaces, etc.) could also be produced. This technology has been used with wax paper, thin metal ribbons and with a variety of thin thermoplastic sheets. However, this technology has not been widely used with ceramic tapes.

Ceramics are a class of materials from which the formation of a three dimensional object from laminations appears to be particularly well suited.

Ceramic materials offer a wide range of attractive engineering properties. For example, their thermal conductivity can be very low (e.g. vitreous $SiO_2$) or very high (e.g., AlN). Some are excellent electrical insulators (e.g. $Al_2O_3$) while others are semiconductors (e.g. SiC) or show metallic conductivity (e.g. $TiB_2$). Structurally, many show good corrosion resistance. Increasingly, ceramics are being developed with high fracture toughness and strength (e.g. partially stabilized $ZrO_2$ and $Si_3N_4$).

Advances in ceramic science achieved during the last decade, have yielded materials with markedly improved properties. Generally, however, these materials have not been successfully transitioned into engineering components. To some extent, this is due to the high capital cost associated with the production of small numbers of ceramic components. It is also due to the fact that ceramics are difficult to process into complex three dimensional objects via the conventional ceramic processing techniques.

In conventional ceramic processing, such as will be described below, a single process is used to determine both the geometry of the object and the microstructure of the powder compact. The term "ceramic processing" is generally interpreted as the entire sequence of steps from the synthesis of a powder of a well defined chemical composition through to the production of a dense material with a well defined microstructure. Virtually all successful processing schemes for engineered ceramics involve powder processing. One characteristic of powder processing is that the shaping of the ceramic part is carried out at a different time than the densification or microstructure development of the ceramic part. Critical to the design of a successful ceramic processing scheme is compatibility between the unit operation which defines the shape of the part to yield a powder compact and the subsequent thermal processing, i.e. binder burnout and sintering.

It is generally recognized that there are three broad classes of ceramic forming processes. These are pressing, plastic forming and casting. Pressing includes both die pressing and isostatic pressing. The principal difference between the two is that die pressing employs hardened steel dies and usually the stress is applied in only one direction. Isostatic pressing uses flexible rubber tooling and the pressure is applied hydrostatically. Both processes use powder particles or granules combined with a binder that is generally solid under the conditions used for pressing. The mass is generally flowable to allow ease of die filling. The powder is poured into a cavity and pressure sufficient to form a cohesive unit is applied. Pressing has a number of advantages, including high throughput, the maintenance of close tolerances and essentially no drying shrinkage. For these reasons, pressing is a widely used method for producing ceramic powder compacts.

However, there are several limitations to pressing. Pressing requires tooling made of hardened steel which is expensive and such investment can only be justified if there are large numbers of pieces to be fabricated. More fundamentally, pressing has inherent geometry limitations since the pieces must be capable of being ejected after pressing. Therefore, neither re-entrant surfaces nor complicated internal geometries can be formed using pressing. In addition, it is well documented that friction between the die wall and the powder mass causes substantial variations in the effective pressure on the powder mass. Such variations in pressure result in density gradients in the powder compact and if they are sufficiently large, the compact is unsuitable for densification. Thus, even for parts of simple geometry, pressing may be unusable. Finally, it is often the case that the pressures used during pressing are insufficient to completely break down the granules of the ceramic and the residue of such granules can be strength limiting flaws. Therefore, pressed ceramic parts often have modest structural performance.

Plastic forming techniques for ceramic parts include extrusion, jiggering and injection molding. Formulations for plastic forming involve the use of a carrier fluid that is present in an amount sufficient to fill the pore space between the ceramic powder particles. The carrier fluid for extrusion and jiggering is usually water. For injection molding, the carrier fluid is often a thermoplastic material which becomes fluid only when heated. Generally, the mixture resists deformation under gravity, but flows readily under moderate external forces. Therefore, pressure is applied to the mixture in order to cause it to flow through a die, such as an extrusion die, or into a cavity for injection molding. When the pressure is removed, the mixture retains the shape of the tooling. With injection molding, the mixture is typically cooled within the mold to allow the mixture to be solidified before ejection. In the case of jiggering, the mixture is compressed between the surface of a permeable die and a roller tool. Some of the liquid is forced out through the permeable die during the shaping process and the stiffness of the mixture is increased. In both extrusion and jiggering, high shear forces can be induced during shaping which increases the uniformity of the powder compact.

However, both extrusion and jiggering are subject to severe geometrical restrictions. In the case of extrusion, only pieces of constant cross-section can be produced. In the case of jiggering, only bodies of revolution can be produced.

Injection molding of ceramic materials can be used to make complicated shapes, but constraints related to geometry still occur. Similar to the case of pressing, neither re-entrant surfaces nor complicated internal geometries can be formed using injection molding. Further constraints on injection molding include the difficulty of fabricating thick walled pieces because of sink marks or cracking which occur due to shrinkage of the carrier fluid during cooling. Also, because the formed piece retains the solidified carrier, it is a dense composite material rather than being a porous powder compact. Binder removal from such a piece represents a serious technical challenge. Extreme procedures are necessary to avoid the generation of internal flaws or warpage of the piece.

Casting processes involve the use of a large amount of carrier fluid in which individual ceramic particles are dispersed to form a slurry. A cast is produced by locally removing some of the carrier fluid. The principal casting process used for ceramic components of complex shape is slip casting and its variants, such as pressure casting or vacuum casting. This process involves filling the cavity of a porous mold with the slurry and extracting the carrier fluid through the pores of the mold—by capillary pressure or applied pressure—allowing a cast to build up on the internal surface of the die. Slip casting is used to make complicated hollow and solid shapes and generally produces very uniform particle compacts.

However, the soft friable, or readily crumbled, nature of the porous mold—which is often slightly soluble in the carrier fluid—limits the dimensional accuracy of the product produced, as well as the service life of the mold. In addition, it is necessary to remove the molded pieces before much drying shrinkage has occurred. Since it is common for the wet strength of the as-cast pieces to be modest, the likelihood of distortion of these pieces during handling is increased. An additional limitation of slip casting is associated with the fact that the rate of build-up of the cast is uniform. Therefore, this technique cannot be used to fabricate hollow shaped bodies of non-constant wall thickness.

The present invention contemplates a new and improved method and apparatus of manufacturing an integral three dimensional object from laminations of a ceramic material which overcomes the foregoing difficulties. The method relies on the separation of the processing steps which control particle packing from those which determine the shape of the component and those which render the powder compact monolithic. The method offers the possibility of producing ceramic powder compacts that 1) have very uniform particle packing; 2) have very low internal stress gradients; 3) are of an arbitrary external shape; 4) have an arbitrary internal geometry; 5) are formulated for ease of binder burnout; 6) require no tooling, and 7) can be functionally graded.

SUMMARY OF THE INVENTION

In accordance with the present invention, a method is provided for manufacturing an integral three dimensional object from laminations.

More particularly in accordance with this aspect of the invention, the method comprises the steps of fabricating a plurality of first sheets of a first material composition, cutting each of the first sheets to form a contoured layer representing a cross-section of the three dimensional object and to form a waste material and discarding the waste material. The contoured layers are stacked in the desired sequence to form a stack of contoured layers. The stack of contoured layers is then laminated. Subsequently, the contoured layers of the stack are secured to each other to form an integral three dimensional object.

According to another aspect of the invention, an apparatus is provided for forming an integral three dimensional object from laminations.

More particularly in accordance with this aspect of the invention, a first station is provided for supplying a first laminate material in the form of a plurality of first sheets and a second station is provided for supplying a second laminate material in the form of a plurality of second sheets. A cutting means cuts the plurality of first and second sheets to contoured layers. An assembly means assembles the contoured layers of the first and second sheets into the form of a three dimensional object. A control means controls the operation of the cutting means and the assembly means. A securing means is then used to secure the plurality of contoured layers of the first and second sheets to each other to complete the formation of the integral three dimensional object.

One advantage of the present invention is the provision of a new and improved method of manufacturing an integral three dimensional object from laminations.

Another advantage of the present invention is the provision of a method for producing three dimensional objects from laminations of a ceramic powder material. The method separates the processing steps which control particle packing of the ceramic from those steps which determine the shape of the object produced and from those steps which render the powder compact monolithic.

A still further advantage of the present invention is the provision of a method for manufacturing an integral three dimensional object from ceramic powder compacts which have very uniform particle packing and very low internal stress gradients. The three dimensional objects so produced can have an arbitrary external shape and an arbitrary internal geometry without the need for any tooling.

A further advantage of the present invention is the provision of an apparatus for forming an integral three dimensional object from laminate sheets of a ceramic material and a fugitive material. These sheets are suitably cut and stacked in a desired sequence so as to form a three dimensional object wherein the voids or empty spaces in the final three dimensional ceramic object are filled temporarily by the fugitive material until the ceramic material is fired.

Still further advantages of the present invention will become apparent to those of ordinary skill in the art upon the reading and understanding of the following detailed description of the preferred embodiments.

BRIEF DESCRIPTION OF THE DRAWINGS

The invention may take form in various parts and arrangements of parts or in various steps and sequences of steps.

The figures and the described structures and methods are only for purposes of illustrating the preferred embodiments of the invention and are not to be construed as limiting same. In the figures.

DETAILED DESCRIPTION OF THE PREFERRED EMBODIMENTS

FIGS. 1–5 illustrate the novel solid freeform fabrication (SFF) method according to the present invention. This method allows a direct fabrication of components of nearly arbitrary complexity using engineering ceramics of arbitrary composition without the need for tooling.

The roots of the current approach lie in the fabrication of multi-layer ceramic substrates for microelectronic packaging. In such substrates, complex internal wiring is created by stacking thin sheets of ceramic powder distributed in a porous polymer matrix which is uncured (a so called "green tape"). The sheets are punched and screen printed with powdered metal inks. The processing of such substrates while representing some of the most advanced ceramic processing available today, is geared toward mass production of a single design. In contrast, the present invention is directed to a true SFF technique which is capable of producing arbitrary one of a kind components.

While the present invention is focused on the use of ceramic materials in the SFF method, it should be apparent to those of average skill in the art that the technology could be extended to the production of both metallic and engineering plastic components as well. Alternatively, the material of the laminates could be made from a mixture of ceramic and metallic or ceramic and plastic materials. In addition, three dimensional object could be made from laminates of different materials, if that is considered desirable.

Figure 1:
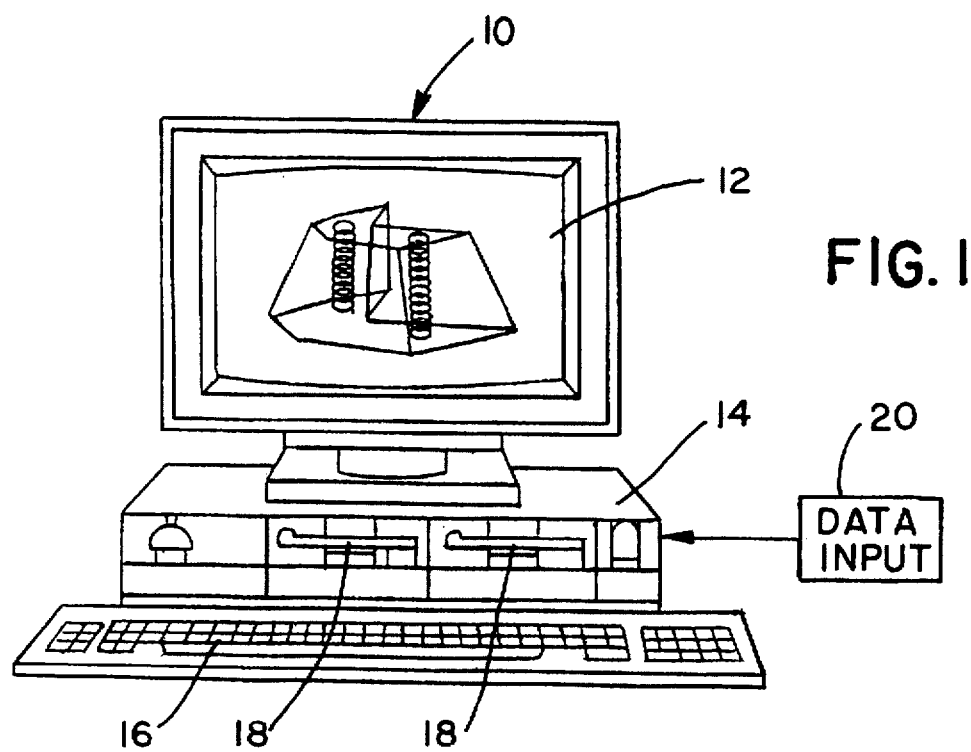
FIG. 1 is a front elevational view of a computer modeling the three dimensional object which is to be produced according to the method of the present invention.

With reference now to FIG. 1, a computer 10 used in connection with the method and apparatus according to the present invention, includes a CRT screen 12 and a console 14 which includes a central processing unit, a RAM memory, an I/O board and data storage capability in the form of a hard drive, as is well known in the art. A keyboard 16 communicates with the I/O board in the computer to allow a programming of the computer. One or more diskette drives 18 are provided on the console 14 so as to allow for additional data input. In addition, further data input can be provided by way of a direct link to a suitable additional device, as exemplified in block 20. Such data input can come from, e.g. a conventional contour follower having a sensing head (not illustrated) in order to input information concerning the three dimensional object.

Figure 2:
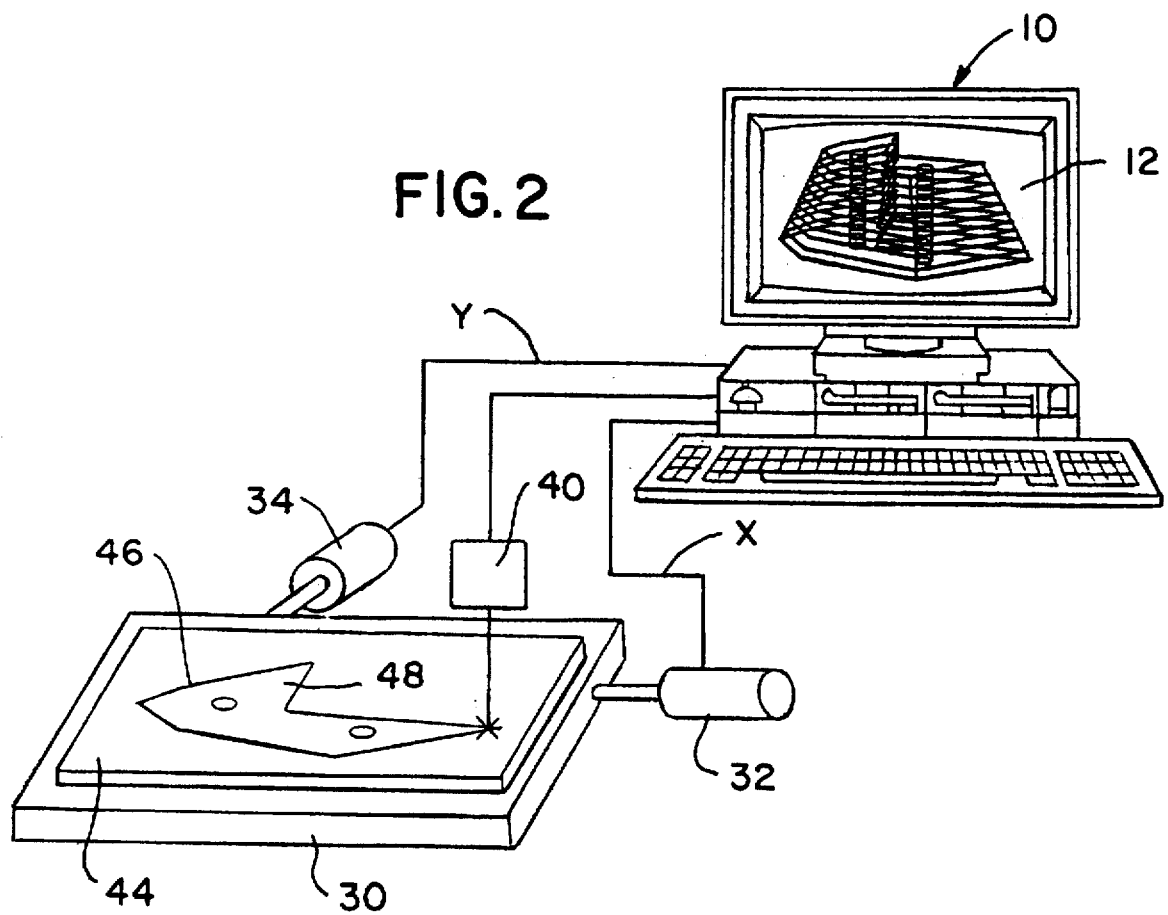
FIG. 2 is a reduced front elevational view of the computer of FIG. 1 showing a contour representation of the three dimensional object with the computer controlling a laser cutting table having a sheet of material from which a contoured lamination is being cut according to the method of the present invention.

With reference now to FIG. 2, the computer 10 controls the operation of an X-Y platform 30 via an X axis control means 32 and a Y axis control means 34. The computer also controls the operation of a laser cutter 40 which cuts a sheet 44 of a suitable desired material, as shown by cut line 46, in order to obtain a suitably contoured lamination 48 of the sheet.

Beam modulation of the laser 40 is coordinated with the trajectory of the X-Y platform 30. For a stationary laser source in the Z direction, cutting platform motions in the X and Y direction are illustrated in FIG. 2. One suitable such platform can be an NEAT 100 mm.×100 mm. travel X-Y platform. The computer 10 can be a SunSparc Station IPC host computer running a VME base multi-processor system for real time control with a variety of conventional pneumatic actuators and controls. The laser 40 can be, e.g., a Coherent General model 42, 50 watt $CO_2$ laser.

However roll and pitch or elevation and azimuth motions would also be possible in order to achieve cutting, not only of outlines but also of edge normals. A fifth degree of freedom is required to coordinate the focus of the laser beam to the height of the cutting point on a tiltable cutting surface. High precision components for constructing such a system are available from a variety of sources including Newport, Aerotech and Anorad. All three suppliers offer rotating tables which can be mounted orthogonally with intersecting axes. Each of the suppliers also provides services for mounting components with a high accuracy of axis parallelism, orthogonality and intersection. A five axis servoed system capable of ten micron translation accuracy (over a 150 millimeter excursion) and an axis alignment within 10 arc seconds can be obtained from any of these vendors.

The sheet 44 is preferably cut from an uncured tape fabricated from a ceramic composition by one of a variety of processes. Such tape is typically produced as a wide sheet, up to 36 inches (91.4 cm.) wide, that is very thin—0.001 inch to 0.01 inch (0.00254 to 0.0254 cm.)—and of arbitrary length.

Tape casting is the most familiar process for the fabrication of high quality ceramic tape with a high degree of flatness. In this process, a slurry containing the ceramic powder, an organic binder/plasticizer system and a volatile solvent is distributed using a doctor blade on an impervious surface. The suspension medium is rapidly evaporated, yielding an elastic, leathery tape which is tough, strong and amenable to cutting and lamination. Tape casting is the preferred technique for thin tapes and may be used down to thicknesses approaching one or two mils, 0.001–0.002 inches (25 to 50 microns).

Another known process is extrusion calendaring which employs a mixture of ceramic powders with binders and plasticizers but no solvent. The batch constituents are premixed and then fed into a high energy mixer. Frictional heating results in a rubbery mixed mass with the consistency of a paste which is passed through a roller mill to form tape. Tape thickness is controlled by adjusting the roller spacing. This process shares some significant features with that used in the production of macrodefect-free cement, i.e. the high shear field in the rolling operation breaks down agglomerates and removes voids.

The third conventional way of ceramic forming to produce tape is via roll compaction. This method employs spray dried granules of ceramic powders with a lower volume fraction of binders and plasticizer. The granulated material is gravity fed between two horizontal rollers. As the powder mass passes between the rollers, it is compressed to form a tape and air is expelled upwards through the loose powder. Breakdown of the granule structure occurs since one characteristic dimension is small and the shear field between the rollers is high.

With any of these three known processes, individual sheets of uncured ceramic tape can be produced with a very uniform particle distribution and in a flaw-free manner. The tape thus produced is then cut by conventional means into sheets 44 of appropriate length.

A preferred type of ceramic material for the sheet 44 can be a green or unfired sheet of a high (about 92% to 96%) aluminum oxide or alumina, $Al_2O$, ceramic manufactured by Coors Electronic Materials (Chattanooga, Tenn.) under the product numbers AD92-96. $Al_2O_3$ is the most widely used technical ceramic with a combination of optical, thermal electrical, chemical and mechanical properties to meet a wide range of engineering applications. However, tapes based on other raw materials are also suitable. One such raw material is an A16-SG alumina available from Alcoa Corporation of Pittsburgh, Pa. Each of these materials is then combined in a slurry with a combination of acrylic emulsion binders (available from Rohm & Haas of Springhouse, Pa. under the B-1000 product number series) and dispersant available from Rohm and Haas under product number D-05. In some cases, a polypropylene glycol emulsion can be added as a plasticizer.

As illustrated in the CRT screen 12 of FIG. 2, any three dimensional object can be broken down into a series of parallel thin sheets with contoured edges and, in principle, the process can be reversed. That is, any arbitrary three dimensional object can be built up from a series of parallel thin sheets with contoured edges. Thus, a set of uncured sheets 44 can be cut to form profiled sections 48 which can be assembled to build a desired shape. In theory, there should be no limitations on the geometry of the final three dimensional object which can be assembled from the several laminations provided by a series of sheets.

Figure 3A:
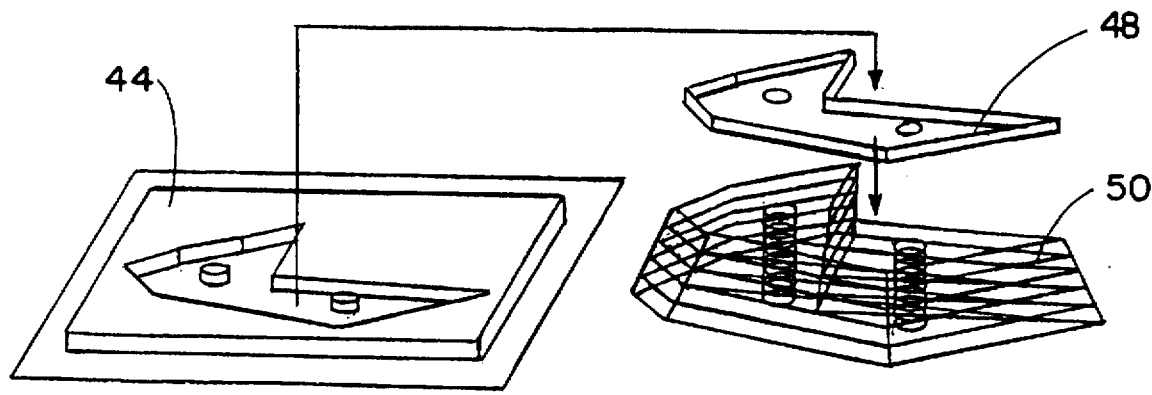
FIG. 3A is a perspective view illustrating the step of stacking the contoured laminations in a desired sequence to begin to form the three dimensional object according to the method of the present invention.

With reference now to FIGS. 3A–3D, the assembly of the outlined and contoured sections 48 into the geometry of the desired three dimensional object simply requires a stacking of the sections 48 with the proper registration. To this end, FIG. 3A illustrates a contoured layer 48 being stacked on a plurality of subjacent contoured layers to form a stack 50 of layers.

The assembly operation includes a "tacking" procedure which fixes the position of each layer relative to the pre-existing stack. Tacking can include the application of a thin adhesive layer between the contoured layers 48 of the sheet. Alternatively, tacking can include the application of a small amount of a solvent, such as ethanol, for the tape binder between the layers. A roller can be used atop the contoured layer 48 to spread the adhesive or solvent, express extra adhesive or solvent, and fix the position of the contoured layer 48 relative to the stack 50. Alternatively, or in addition, a gripper can be used to place a small downward force to preserve the integrity of the stack and the exposed sides can be coated with an adhesive, such as rubber cement, to insure that the several layers do not move in relation to each other during the handling of the stack 50.

Figure 3B:
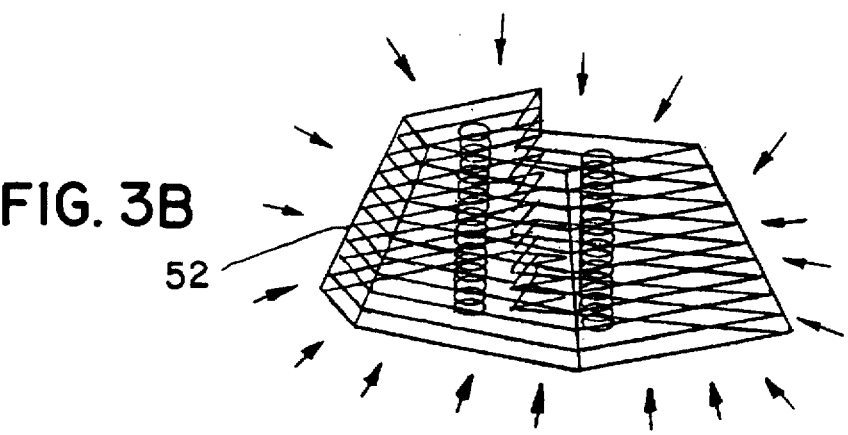
FIG. 3B is a perspective view illustrating the step of isostatically pressing the laminations of the three dimensional object.

With reference now to FIG. 3B, after assembly, the layers of the stack 50 are "laminated" by, e.g. uniaxial pressing or another suitable method to compress the layers 48 somewhat and achieve intimate interlayer contact promoting a high integrity bonding in the subsequent sintering operation. As is known in the art, a vacuum may be pulled on the stack before pressing.

Isostatic pressing is widely employed in ceramic forming. Typically, the part is placed in an impermeable bag, which is the evacuated, sealed and submerged in a hydraulic pressure vessel. Often, the fluid is at room temperature—so called cold isostatic pressing—but it can be heated—warm isostatic pressing—. For example, the isostatic pressing can take place at a temperature of BOOC and a pressure of 700 psi. Alternatively, such isostatic pressing can take place at ambient temperature at a pressure of 15,000 psi.

Figure 3C:
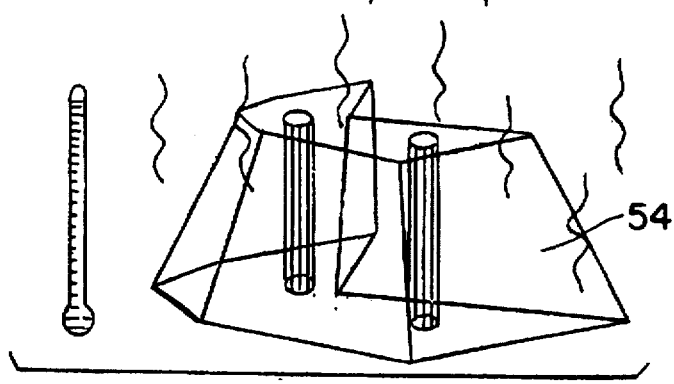
FIG. 3C is a perspective view illustrating the step of firing ceramic material of the laminations of the three dimensional object.

Two issues which arise during firing of the ceramic mass, as illustrated in FIG. 3C, are the ease of binder removal and the extent to which shrinkage can be controlled. Standard firing schedules can be used to successfully remove the binder. Laminating the ceramic tape layers yields a uniform polymer/ceramic composite with a relatively high volume fraction of binder but which also contains continuously connected pores to allow binder burnout using a straightforward controlled firing schedule. Shrinkage is comparable to those encountered when using powder compacts derived from conventional ceramic forming operations.

It is possible, in principle, to compensate for the shrinkage of the laminated layers during firing by prescaling the dimensions of the individual layers to the desired size. Roughly, a 15% shrinkage of the uncured ceramic tape is expected during post-process densification, depending to some extent on the specific tape formulation. While such a shrinkage is considerable, when it is sufficiently uniform and reproducible, uncured assemblies can be fabricated with correspondingly scaled up dimensions to achieve the desired final dimensions of the fired parts.

Figure 3D:
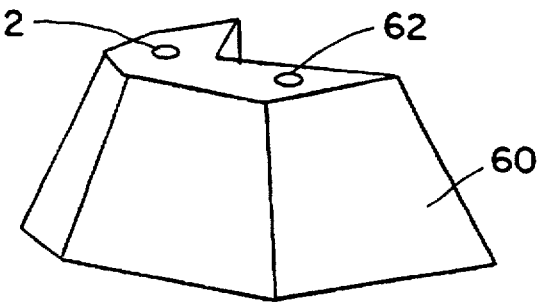
FIG. 3D is a perspective view of the finished three dimensional object.

After the firing operation, a final object 60 is created, as illustrated in FIG. 3D. It is evident that the object has a complex three dimensional shape with voids 62 extending through the object.

Isostatic pressing can be very difficult if the three dimensional object, which is to be formed, is delicate or is of a complex shape. For this reason, it may be advisable to employ not only sheets of a ceramic material, but also sheets of a fugitive material in the lamination which forms the object. In this regard, attention is drawn to FIG. 4. This figure illustrates the use of a fugitive tape, together with a ceramic tape, to achieve the formation of the final object.

Figure 4:
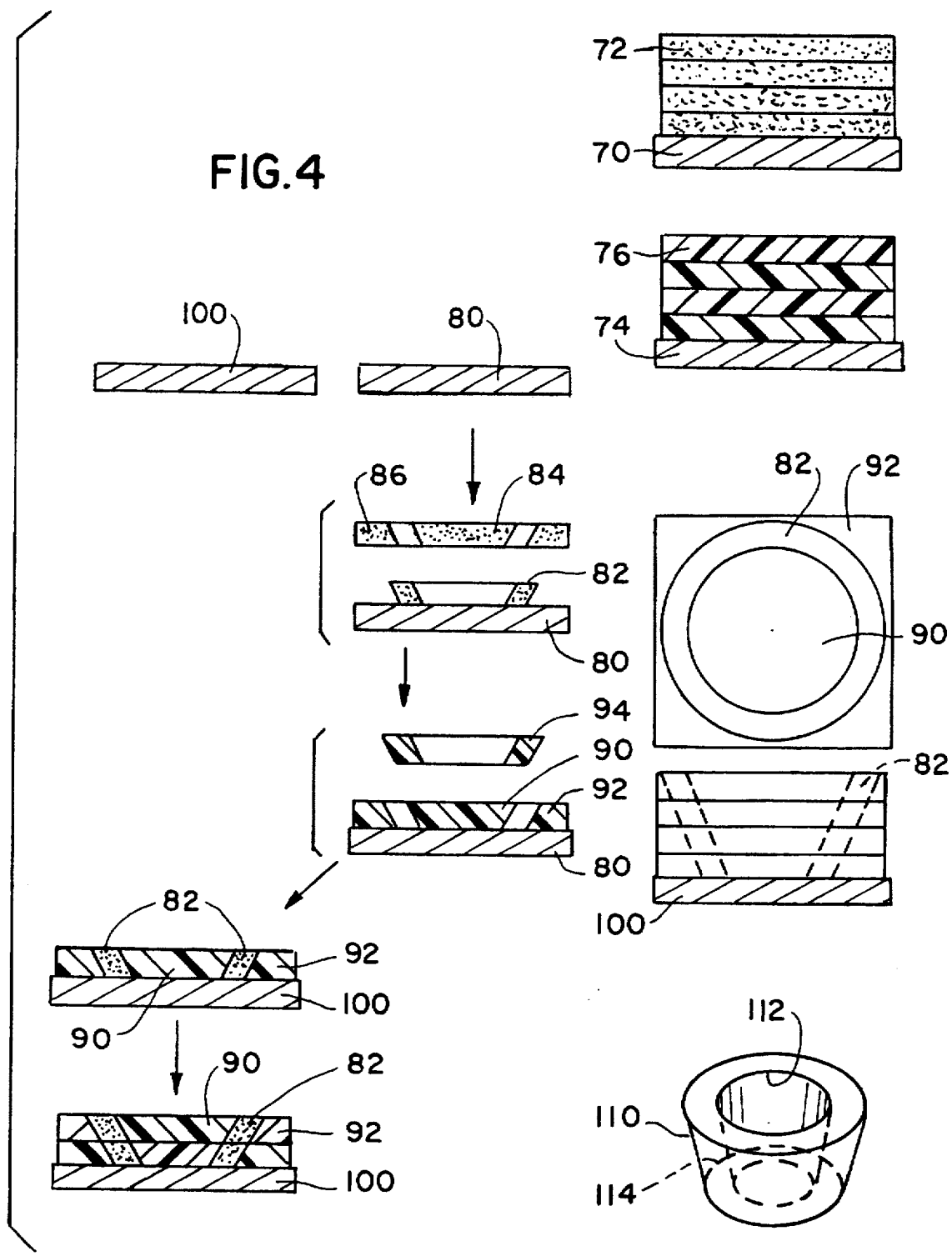
FIG. 4 is a schematic view of the several steps needed to manufacture an integral three dimensional object from laminations when using a fugitive tape to provide support for the void areas in the several layers of the contoured ceramic material laminate from which the finished part is produced, according to the present invention; and, FIG. 5 is a block diagram view illustrating the steps involved in the method illustrated in FIG. 4 for manufacturing a three dimensional object according to the present invention.

FIG. 4 illustrates a first supply table 70 which has on it a plurality of ceramic sheets 72 cut from tape. There is also provided a second supply table 74 which has on it a plurality of fugitive sheets 76 cut from tape. At a cutting table 80, the ceramic sheets 72 are cut by a laser cutter or the like, as illustrated in FIG. 2. The fugitive tape serves as a temporary support means in order to allow the formation of surfaces with downward pointing surface normals, e.g. cantilevers, "ceilings," "stalactites," etc. The fugitive layers support the uncured assemblies. Fugitive layers are laser cut from sheet stock generating shapes complementary to the respective desired part cross-sections.

The ceramic sheets 72 are so cut that a ring portion 82 is kept whereas a central section 84 is discarded, as is a peripheral section 86. The fugitive sheets 76 are so cut that a central section 90 is kept, as is a peripheral section 92, whereas a ring section 94 between them is discarded. Subsequently, the ceramic and fugitive layers, which have been kept, are assembled together on an assembly platform 100. Fugitive tapes and the ceramic tapes are cut alternately enabling the construction of layered assemblies of solid blocks with spatially varying material properties. There are advantages to fabricating a powder compact with simple external shape despite the fact that final component after firing will have one or more of the following: complex external shape, including concavities; internal passages; hollow cavities. It is for this reason that the fugitive tape is placed in the regions that, after firing of the ceramic, will be ultimately empty. A plurality of such layers are placed on the assembly platform until the requisite number of layers has been obtained to create the final three dimensional product.

The assembly of the outlined and contoured sheets into the geometry of the final desired object simply requires a stacking of the layers with the proper registration.

The fugitive material must satisfy a number of different constraints in order to effectively serve its role as a mechanical support during both assembly and any post-assembly lamination process. The fugitive layers must allow the forming of a flat surface coplanar with the surface of the subassembly after each layer is stacked. The fugitive material itself should closely match the thermal and elastic properties of the uncured ceramic material so that the thermal stresses applied during subsequent heating and distortion under the application of pressure are minimized. Finally, it is important that the fugitive material can be completely removed prior to the onset of densification during firing, without causing delamination or the introduction of other flaws. There are at least two classes of material that can be used as a fugitive. The first is an organic material which burns out during the initial stage of firing. The second is a green tape made from an inorganic powder that resists sintering due, either to its coarse size or its chemical makeup. Such a tape will be converted to a loose powder during firing.

There are several classes of organic material which are useful as fugitive material. These include acrylic latex, which is readily available as colloidal suspensions, walnut flour made by grinding walnut shells and organic gels. Another useful material for this purpose is a corn starch. A chemical grade corn starch is available from Sigma Chemicals of St. Louis, Mo. The starch can be layered into a tape either in an aqueous based slurry or in non-aqueous slurries using toluene or polyvinyl butyrate.

Inorganic powders that are suitable for use as fugitive material include oxide ceramic powders coarser than 3 μm, and submicron or coarser nonoxide ceramic powders when fired in a reducing atmosphere. In contrast to the laminate sheet material made of a polymer/ceramic composite—in which the particle size of the ceramic powder can be on the order of one-half micron—the ceramic powder in the fugitive polymer/ceramic composite material can be on the order of, e.g. 10 microns. While the smaller particle size ceramic powder in the laminate tape material fuses during the sintering process, the larger size ceramic powder in the fugitive material does not so fuse. As the binder is burned away from both the laminate material and the fugitive material, the fugitive material becomes merely a mass of powder that can and does flow.

The several sheets which are placed on the assembly platform 100 can be rendered monolithic through a variety of procedures. These include the application of a thin adhesive layer between sheets or the application of a small amount of a solvent—for the binder used in the laminate sheets—between the sheets. Alternately, a pressure can be applied sufficient to cause the binder to adhere to the binder in the neighboring sheet. If desired, the temperature can be raised when a thermoplastic binder is used in order to tack the sheets to each other. Of course, some combination of the above-listed four procedures can also be used.

For purposes of registration, it may be desirable to use registration pins or spots of adhesive and low pressure during stacking. This is followed by a single cycle of high pressure and/or elevated temperature in order to render the stack monolithic. As mentioned with regard to FIG. 3C, the object is placed in a furnace and heated in order to break down the fugitive material and fuse the sinterable ceramic material into a structurally solid final object 110. As is evident, the object 110 has a tapered central opening 112 and a tapered outer periphery 114.

The flowable powder produced by thermal decomposition of the fugitive containing an inorganic powder can be easily removed through gentle mechanical action or ultrasonic vibration of a liquid bath in which the body is immersed. Such shaking of the body will cause the powder, which now comprises the fugitive material, to fall away from the body through an opening in the body. It may be necessary to have a hole left in the outer periphery of the body through which the fugitive material can be removed. If a completely enclosed void is formed in the body, then only an organic fugitive tape material can be used. Once the powder has been removed from the hole in the body, the hole can be plugged via any suitable conventional means.

Figure 5:
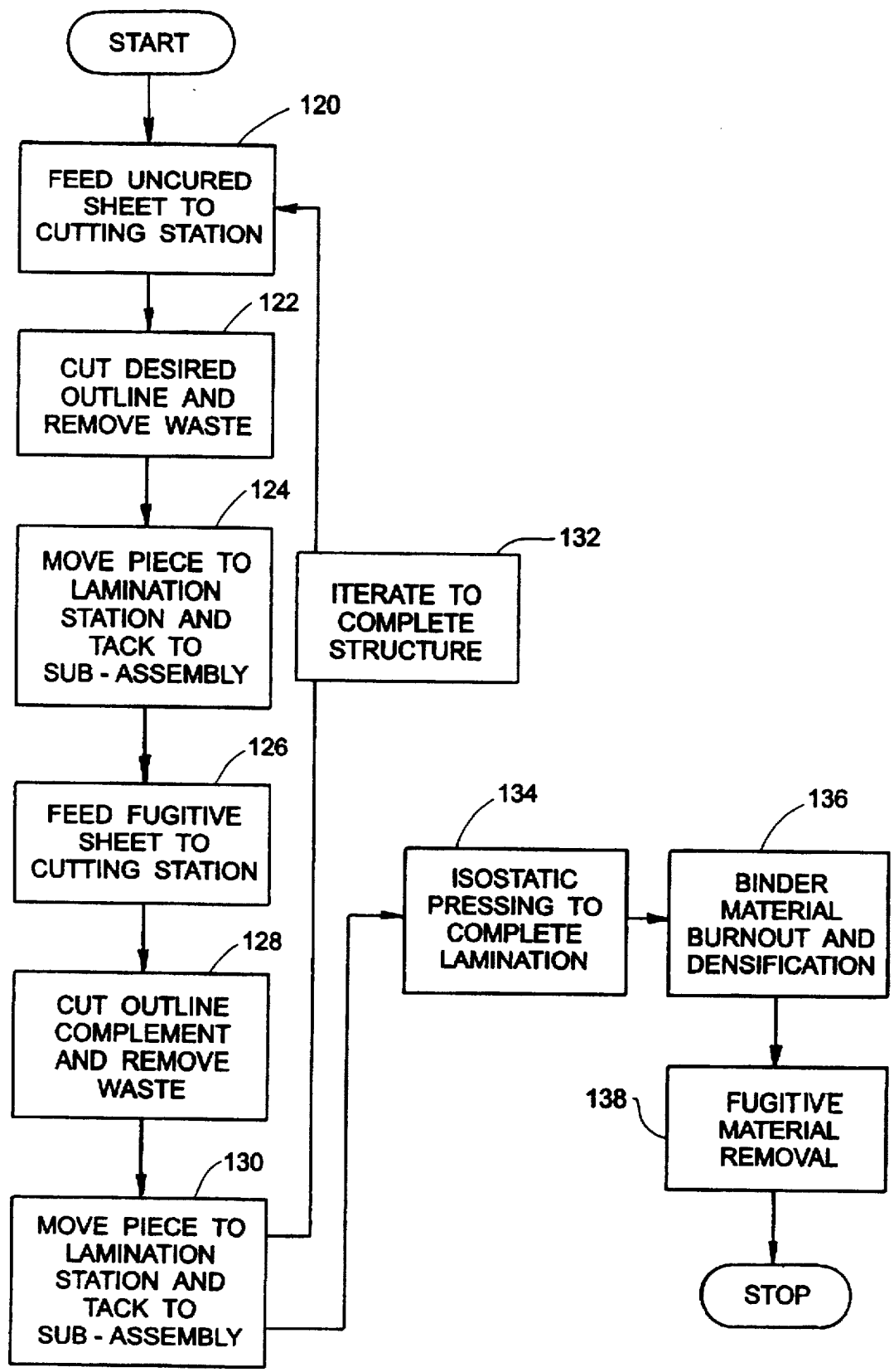

FIG. 5 illustrates in block diagram form the method steps which are performed in the schematic process outlined in FIG. 4. An uncured ceramic sheet 72 is fed to a cutting station as shown in block 120. The desired outline is cut from the sheet and the waste is removed, as illustrated in block 122. The pieces then move to the lamination station and are tacked to the subassembly, as shown in block 124. A fugitive sheet 76 is also fed to the cutting station as shown in block 126. The outline complement is cut in the fugitive sheet as shown in block 128 and the fugitive sheet piece is moved to the lamination station and tacked to the subassembly as illustrated in block 130. These method steps are repeated, as illustrated in block 132, until the complete structure has been constructed. Thereafter, the structure undergoes an isostatic pressing to complete its lamination as illustrated in block 134. Finally, as illustrated in block 136, the binder is burned out and the fugitive material is burned out or broken down, the ceramic material densities to form the final desired object and the fugitive material is removed (see block 138).

The process outlined above promises to yield an improved ceramic powder compact for a number of reasons. First, the homogeneity of particle packing and ease of binder burnout can be controlled during the primary operation to fabricate the tape. For instance, tape casting allows a tape of exceptional homogeneity to be fabricated. Such tapes contain on the order of 65 vol. % ceramic powder, 15 vol. % binder and 20 vol. % porosity. This level of porosity provides for sufficient venting during binder burnout.

Second, with suitable lamination processes, the maximum stress applied to the compact can be both low and uniformly applied. This results in very low stress gradients and thus minimizes internal stress. Third, arbitrary wall thicknesses can be cut in the individual sheets so that powder compacts of widely varying cross-section can be fabricated. Fourth, internal geometries can be defined when fugitive tapes are interleaved with the ceramic engineering material tapes, as is illustrated in FIG. 4.

Fifth, similar fugitive tapes can be placed around the object so as to form a shell around the entire external surface of the object in order to provide a protective structure for handling. This is also illustrated in FIG. 4. Sixth, the absence of rigid tooling should result in a unit cost that is a weak function of production volume thus offering low cost powder compacts for the purpose of design iteration, dimensional refinement and small volume production runs.

Seventh, the process according to the present invention provides for the possibility of functionally grading the final component. That is, material properties can be improved because successive layers of the final object can be made of different materials. Alternately, partial layers can be combined to yield novel laminated microstructures. For example, the materials may differ in composition, e.g. alumina/alumina-zirconia or metal-ceramic. Alternately, the materials may differ only in microstructure, such as dense/porous silicon nitride.

The present invention allows the fabrication of solid components of complex internal and external geometry from laser cut sheet stock. In the present invention, pre-processed laminae that are stacked into laminated assemblies which are then post-processed into fully functional components. A cut, then laminate approach is used for each lamina. This permits ready fabrication of composites and components with complex internal geometry.

With the present invention, it is now possible to process ceramics with both complex internal and external structures allowing both controlled microstructures and complex void patterns to be developed. It also allows the fabrication of laminated composites which permit entirely new applications for ceramics. By working with sheet materials, one is able to perform solid free-form fabrication directly in a wide array of engineering materials other than ceramics as well. It should be recognized, however, that the post shaping processes for securing the several contoured layers together will differ depending upon the material composition of the layers.

All of the above discussion relates to the formation of green powder compacts that employ a ceramic as the inorganic powder, are laminated by thermocompression and use heating to decompose the fugitive material. However, it is recognized that the advantages of this invention are directly extensible to the fabrication of green powder compacts made using metallic powders, and to engineering plastics in sheet form. Furthermore, the lamination may involve any of a variety of well established methods, such as adhesive lamination. Finally, other methods for removal of the fugitive material will be obvious to those skilled in the art, such as solvent extraction and the like.

The aforesaid method and apparatus according to the present invention can be employed to manufacture engineering prototypes. However, it can also be used to manufacture molds and dies for the process of manufacturing objects. In addition, it can be employed to fabricate prosthetic implants to replace, e.g., the hard tissue of a person or an animal. For example, a dental implant or a replacement bone can be manufactured with the method and apparatus according to the present invention.

The invention has been described with reference to preferred embodiments. Obviously, modifications and alterations will occur to others upon the reading and understanding of the preceding specification. It is intended that the invention be construed as including all such alterations and modifications insofar as they come within the scope of the appended claims or the equivalents thereof.

We claim:

1. A method of manufacturing an integral three-dimensional object from laminations, comprising the steps of:

fabricating a plurality of first sheets of a first material composition;

fabricating a plurality of second sheets of a second material composition;

cutting each of said first sheets to form a contoured layer representing a cross-section of the three-dimensional object and to form a waste material;

cutting each of said second sheets to form a contoured layer representing a void in a cross-section of the three-dimensional object and to form a waste material;

discarding the waste material of said first and second sheets;

stacking said contoured layers of said first and second sheets in a desired sequence to form a stack of contoured layers;

laminating said stack of contoured layers; and, subsequently securing said contoured layers of said stack to each other to form an integral three dimensional object.

2. The method of claim 1 wherein said step of securing comprises the subsidiary step of heating the material composition of said stack of contoured layers.

3. The method of claim 1 further comprising the step of decomposing said contoured layers of said second material, said step of decomposing taking place after said step of securing.

4. The method of claim 1 further comprising the step of combusting said contoured layers of said second material, said step of combusting taking place during said step of securing.

5. The method of claim 1 wherein said step of securing comprises the subsidiary step of depositing a layer of adhesive between each of said contoured layers of said stack.

6. The method of claim 1 wherein said step of securing comprises the subsidiary step of depositing a layer of solvent between each of said contoured layers of said stack.

7. The method of claim 1 wherein said step of securing comprises the subsidiary step of raising a temperature of said stack of contoured layers.

8. The method of claim 1 wherein said step of securing comprises the subsidiary step of exerting a pressure on said stack of contoured layers.

9. A method of manufacturing an integral three-dimensional object from laminations, comprising the steps of:

developing a contour representation of a three-dimensional object;

fabricating a set of first sheets of an uncured inorganic powder material;

cutting each of said set of first sheets to a desired shape, each of said first sheets when cut being a contoured layer representing a cross-section of the three-dimensional object;

fabricating a set of second sheets of a fugitive material;

cutting each of said set of second sheets to a desired shape, each of said second sheets when cut being a contoured layer representing an empty area in the cross-section of the three-dimensional object; and, stacking said contoured layers of said first and second sheets in a desired sequence such that one contoured layer of said first sheets and one contoured layer of said second sheets are stacked at a time;

securing said contoured layers to each other; and, sintering the inorganic powder material of said contoured layers to form an integral body from said contoured layers.

10. The method of claim 9 wherein said step of securing comprises the subsidiary step of depositing a layer of adhesive between each of said contoured layers.

11. The method of claim 9 wherein said step of securing comprises the subsidiary step of depositing a layer of solvent between each of said contoured layers.

12. The method of claim 9 further comprising the step of removing said contoured layers of said second sheets.

13. The method of claim 12 wherein said step of removing comprises the subsidiary step of combusting at least a portion of said contoured layers of said second sheets.

14. A method of manufacturing an integral three-dimensional object from laminations, comprising the steps of:

fabricating a plurality of first sheets of a first material composition;

fabricating a plurality of second sheets of a second material composition;

cutting each of said first sheets to form a contoured layer representing a cross-section of the three-dimensional object and to form a waste material;

cutting each of said second sheets to form a contoured layer representing a void in a cross-section of the three-dimensional object and to form a waste material;

discarding the waste material of said first and second sheets;

stacking said contoured layers of said first and second sheets in a desired sequence to form a stack of contoured layers;

laminating said stack of contoured layers; and, subsequently securing said contoured layers of said stack to each other to form an integral three dimensional object, said step of securing including a step of combusting said contoured layers of said second material; and, removing residual material resulting from said combusting step by applying a mechanical action to the integral three dimensional object.

15. The method of claim 14 wherein said second material comprises a resin and a granular material and wherein said resin material is combusted during said step of combusting but said granular material is not combusted and wherein said granular material is removed from the integral three dimensional object during said step of applying a mechanical action by falling away from the integral three dimensional object.

16. A method of manufacturing an integral three-dimensional object from laminations, comprising the steps of:

developing a contour representation of a three-dimensional object;

fabricating a set of first sheets of an uncured inorganic powder material;

cutting each of said set of first sheets to a desired shape, each of said first sheets when cut being a contoured layer representing a cross-section of the three-dimensional object;

fabricating a set of second sheets of a fugitive material;

cutting each of said set of second sheets to a desired shape, each of said second sheets when cut being a contoured layer representing an empty area in the cross-section of the three-dimensional object;

stacking said contoured layers of said first and second sheets in a desired sequence such that one contoured layer of said first sheets and one contoured layer of said second sheets are stacked at a time;

securing said contoured layers to each other;

combusting at least a portion of said contoured layers of said second sheets and sintering the inorganic powder material of said contoured layers of said first sheets to form an integral body from said contoured layers;

forming a remaining portion of said contoured layers of said second sheets into a granular material;

providing an aperture in the integral body formed from said contoured layers; and, applying a mechanical action to the integral body formed from said contoured layers so that the granular material can fall out through said aperture.

\* \* \* \* \*